United States Patent
Gong et al.

(10) Patent No.: US 11,596,590 B2
(45) Date of Patent: *Mar. 7, 2023

(54) METHODS AND KITS OF REMOVING CALCULUS

(71) Applicant: 3M INNOVATIVE PROPERTIES COMPANY, St. Paul, MN (US)

(72) Inventors: Tao Gong, Woodbury, MN (US); Petra L. Kohler Riedi, Minneapolis, MN (US); Evan Koon Lun Yuuji Hajime, Woodbury, MN (US); Steven P. Swanson, Blaine, MN (US)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 1073 days.

This patent is subject to a terminal disclaimer.

(21) Appl. No.: 16/305,107

(22) PCT Filed: Jun. 21, 2017

(86) PCT No.: PCT/US2017/038471
§ 371 (c)(1),
(2) Date: Nov. 28, 2018

(87) PCT Pub. No.: WO2017/223161
PCT Pub. Date: Dec. 28, 2017

(65) Prior Publication Data
US 2020/0315942 A1 Oct. 8, 2020

Related U.S. Application Data

(60) Provisional application No. 62/353,407, filed on Jun. 22, 2016.

(51) Int. Cl.
*A61K 8/66* (2006.01)
*A61K 8/22* (2006.01)
*A61Q 11/00* (2006.01)

(52) U.S. Cl.
CPC .................. *A61K 8/66* (2013.01); *A61K 8/22* (2013.01); *A61Q 11/00* (2013.01)

(58) Field of Classification Search
CPC ... A61K 8/38; A61K 8/66; A61K 8/81; A61K 8/22; A61K 8/60; A61K 11/00
USPC .................................................. 424/49, 53
See application file for complete search history.

(56) References Cited

U.S. PATENT DOCUMENTS

| | | |
|---|---|---|
| 1,482,367 A | 1/1924 | Elledge |
| 3,372,125 A | 3/1968 | Hill |
| 3,535,421 A | 10/1970 | Briner |
| 3,678,154 A | 7/1972 | Widder |
| 4,155,868 A | 5/1979 | Kaplan |
| 4,381,247 A | 4/1983 | Nakagawa |
| 4,417,993 A | 11/1983 | Gergely |
| 4,522,805 A | 6/1985 | Gordon |
| 4,528,180 A | 7/1985 | Schaeffer |
| 4,894,220 A | 1/1990 | Nabi |
| 5,071,439 A | 12/1991 | Weible |
| 5,403,578 A | 4/1995 | Gordon |
| 5,670,138 A | 9/1997 | Venema |
| 5,908,614 A | 6/1999 | Montgomery |
| 5,965,110 A | 10/1999 | Arnold |
| 6,221,641 B1 | 4/2001 | Montgomery |
| 6,331,291 B1 | 12/2001 | Glace |
| 6,379,654 B1 | 4/2002 | Gebreselassie |
| 6,440,396 B1 | 8/2002 | McLaughlin |
| 6,485,709 B2 | 11/2002 | Banerjee |
| 6,669,929 B1 | 12/2003 | Boyd |
| 6,685,921 B2 | 2/2004 | Lawlor |
| 7,530,808 B2 | 5/2009 | Cao |
| 7,740,479 B2 | 6/2010 | Allred |
| 7,816,423 B2 | 10/2010 | Karim |
| 8,647,608 B2 | 2/2014 | Yang |
| 8,906,981 B2 | 12/2014 | Yang |
| 2002/0141949 A1 | 10/2002 | Banrjee |
| 2003/0194382 A1 | 10/2003 | Chang |
| 2003/0194978 A1* | 10/2003 | Vorenkamp ............... H03F 1/26 455/197.1 |
| 2004/0120900 A1 | 6/2004 | Arsenault |
| 2005/0100514 A1 | 5/2005 | Sakaguchi |
| 2005/0196348 A1 | 9/2005 | Georgiades |
| 2006/0051385 A1 | 3/2006 | Scholz |
| 2006/0099155 A1 | 5/2006 | MacDonald |
| 2006/0198803 A1 | 9/2006 | Giniger |

(Continued)

FOREIGN PATENT DOCUMENTS

| | | |
|---|---|---|
| CN | 104173197 | 12/2014 |
| DE | 1944308 | 3/1971 |

(Continued)

OTHER PUBLICATIONS

Rotstein, "Role of Catalase in the Elimination of Residual Hydrogen Peroxide following Tooth Bleaching." Journal of Endodontics vol. 19, No. 11, Nov. 1993. (Year: 1993).*
Easton, "The behavior of mixtures of hydrogen peroxide and water", Part I. Determination of the densities of mixtures of hydrogen peroxide and water, Trans. of Faraday Soc, 1952, vol. 48, pp. 796-801.
Ilan Rotstein, "Role of Catalase in the Elimination of Residual Hydrogen Peroxide following Tooth Bleaching," Nov. 1993, *Journal of Endodontics*, 19(11): 567-69.

(Continued)

*Primary Examiner* — Walter E Webb
(74) *Attorney, Agent, or Firm* — 3M Innovative Properties Company

(57) ABSTRACT

Methods and kids for removing calculus from a tooth. The method can include applying a component A comprising a hydrogen peroxide or a precursor thereto and a component B the comprising a catalase to the tooth, thereby generating oxygen; and removing at least a part of the calculus from the tooth.

26 Claims, 3 Drawing Sheets

(56) References Cited

U.S. PATENT DOCUMENTS

| | | | |
|---|---|---|---|
| 2007/0190483 | A1* | 8/2007 | Larsen .............. A61C 19/063 433/89 |
| 2009/0220919 | A1 | 9/2009 | Yang |
| 2011/0305738 | A1 | 12/2011 | Ladizinsky |
| 2012/0282234 | A1 | 11/2012 | Min |
| 2017/0367941 | A1 | 12/2017 | Haeberlein |
| 2019/0231649 | A1 | 8/2019 | Kohler Riedi et al. |

FOREIGN PATENT DOCUMENTS

| | | |
|---|---|---|
| FR | 2787778 | 6/2000 |
| GB | 1492660 | 11/1977 |
| JP | 0597640 | 4/1993 |
| JP | 2003-40754 | 2/2003 |
| JP | 2004-091404 | 3/2004 |
| RU | 2432620 | 10/2011 |
| WO | WO 1992-07550 | 5/1992 |
| WO | WO 1998-057653 | 12/1998 |
| WO | WO 2007/037960 | 4/2007 |
| WO | WO 2009-109533 | 9/2009 |
| WO | WO 2012-072777 | 6/2012 |
| WO | WO 2013-055478 | 4/2013 |
| WO | WO 2015-073246 | 5/2015 |
| WO | WO 2016-099875 | 6/2016 |
| WO | WO 2017/223161 | 12/2017 |
| WO | WO 2018-075149 | 4/2018 |
| WO | WO 2018-075150 | 4/2018 |

OTHER PUBLICATIONS

International Search report for PCT International Application No. PCT/US2017/038471 dated Oct. 16, 2017, 4 pages.
"Iodide", Wikipedia, [retrieved from the internet on Jun. 12, 2019], URL <https://en.wikipedia.org/wiki/Iodide>, pp. 1-4.
Bray, "Reactions Involving Hydrogen Peroxide, Iodine and Iodate Ion", Journal of the American Chemical Society, 1931, vol. 53, No. 01, pp. 38-44.
Bull, "Iron-Ethylenediaminetetraacetic Acid (EDTA)-Catalyzed Superoxide Dismutation Revisited : An Explanation of Why the Dismutase Activity of Fe-EDTA Cannot Be Detected in the Cytochrome c/Xanthine Oxidase Assay System", Archives of Biochemistry and Biophysics, 1982, vol. 215, No. 02, pp. 551-555, XP024804756.
Chen, "Dual Enzyme-like Activities of Iron Oxide Nanoparticles and Their Implication for Diminishing Cytotoxicity", ACS Nano, 2012, vol. 06, No. 05, pp. 4001-4012.
Day, "Catalase and Glutathione Peroxidase Mimics", Biochemical Pharmacology, 2009, vol. 77, No. 03, pp. 285-296.
Gao, "Nanocatalysts Promote *Streptococcus mutans* Biofilm Matrix Degradation and Enhance Bacterial Killing to Suppress Dental Caries In Vivo", Biomaterials, 2016, vol. 101, pp. 272-284.
Home Remedies, "Get Rid of Plaque & Tartar on Teeth with Natural Remedies," HomeRemedies.com, Oct. 30, 2009; 3 pages (Year: 2009).
Koo, "A New Cost Effective Approach for Plaque Control and Tooth Decay Prevention", Penn Center for Innovation, [retrieved from the internet on Jun. 12, 2019], URL < http://upenn.technologypublisher.com/technology/22598 >, p. 1.
Kraus et al., "Salivary Catalase and Peroxidase values in Normal Subjects and in Persons with Periodontal Disease." O.S, O.M, & O.P. Jan. 1958; vol. 11, No. 1; pp. 95-102 (Year: 1958).
Livingston, "The Catalytic Decomposition of Hydrogen Peroxide in an Acid Chlorine-Chloride Solution", Journal of the American Chemical Society, 1925, vol. 47, No. 08, pp. 2069-2082.
Nardello, "Identification of the Precursor of Singlet Oxygen ($^1O_2$, $^1\Delta g$) Involved in the Disproportionation of Hydrogen Peroxide Catalyzed by Calcium Hydroxide", Chemical Communications, 1998, vol. 05, pp. 599-600.
Nardello, "Inorganic Compounds and Materials as Catalysts for Oxidations With Aqueous Hydrogen Peroxide", Journal of Molecular Catalysis. A Chemical, 2006, vol. 251, No. 1-2, pp. 185-193, XP028015283.
Putt et al., "Custom Tray Application of Peroxide Gel as an Adjunct to Scaling and Root Planing in the Treatment of Periodontitis: Results of a Randomized Controlled Trial after Six Months." J Clin Dent 2013;24:100-107 (Year: 2013).
Rauen, "Conversion of the Synthetic Catalase Mimic Precursor TAA-1 into the Active Catalase Mimic in Isolated Hepatocytes", Chemical Biology and Drug Design, 2009, vol. 73, No. 05, pp. 494-501.
Signorella, "Bioinspired Functional Mimics of the Manganese Catalases", Coordination Chemistry Reviews, 2012, vol. 256, No. 11-12, pp. 1229-1245.
Tovmasyan, "A Comprehensive Evaluation of Catalase-Like Activity of Different Classes of Redox-Active Therapeutics", Free Radical Biology and Medicine, 2015, vol. 86, pp. 308-321.
Wahlen, "Disproportionation of Hydrogen Peroxide Into Singlet Oxygen Catalyzed by Lanthanum-Exchanged Zeolites", Journal of Catalysis, 2005, vol. 233, No. 02, pp. 422-433.
Wahlen, "Lanthanum-Doped Zinc Hydroxycarbonates for the Catalytic Disproportionation of Hydrogen Peroxide Into Singlet Oxygen", Journal of Catalysis, 2007, vol. 249, No. 01, pp. 15-23.
Walling, "The lron(III)-Ethylenediaminetetraacetic Acid-Peroxide System", Inorganic Chemistry, 1970, vol. 09, No. 04, pp. 931-937.
Wu, "Structural, Spectroscopic, and Reactivity Models for the Manganese Catalases", Chemical Reviews, 2004, vol. 104, No. 02, pp. 903-938.

* cited by examiner

METHODS AND KITS OF REMOVING CALCULUS

Dental calculus may lead to periodontal diseases including gingivitis and periodontitis. The existing methods of removing dental calculus rely upon mechanical means such as scaling by trained dental professionals. Such existing removal procedures can be painful and uncomfortable for patients. In addition, the existing removal procedures can put a significant physical burden on the hygienist, often times leading to muscular and repetitive movement ailments (e.g., carpal tunnel syndrome). Moreover, a significant amount of time during the dental prophylaxis procedure is allocated to calculus removal. Although various methods for calculus removal are disclosed in PCT Patent Application Serial Number PCT/US2015/063335, "Methods and Kits of Removing Calculus," filed on Dec. 2, 2015, it is always desirable to continue to create better solutions to remove calculus.

BACKGROUND

Summary

Some aspects of the present disclosure provide a method of removing calculus from a tooth. The method can include providing a component A, wherein the component A comprises a hydrogen peroxide or a precursor thereto; providing a component B, wherein the component B comprises a catalase; applying the component A and the component B to the tooth, thereby generating oxygen; and removing at least a part of the calculus from the tooth; wherein component A and component B are each independently a liquid or a gel; and wherein at least one of the component A and the component B has a viscosity of less than 26 Pa·s at a shear rate of 1/s at 25° C.

Some aspects of the present disclosure provide a kit of parts for removing calculus from a tooth. The kit can include a component A comprising a hydrogen peroxide or a precursor thereto; and a component B comprising a catalase; wherein component A and component B are each independently a liquid or a gel; and wherein at least one of component A and component B has a viscosity of less than 26 Pa·s at a shear rate of 1/s at 25° C.

DETAILED DESCRIPTION

Figure 1:
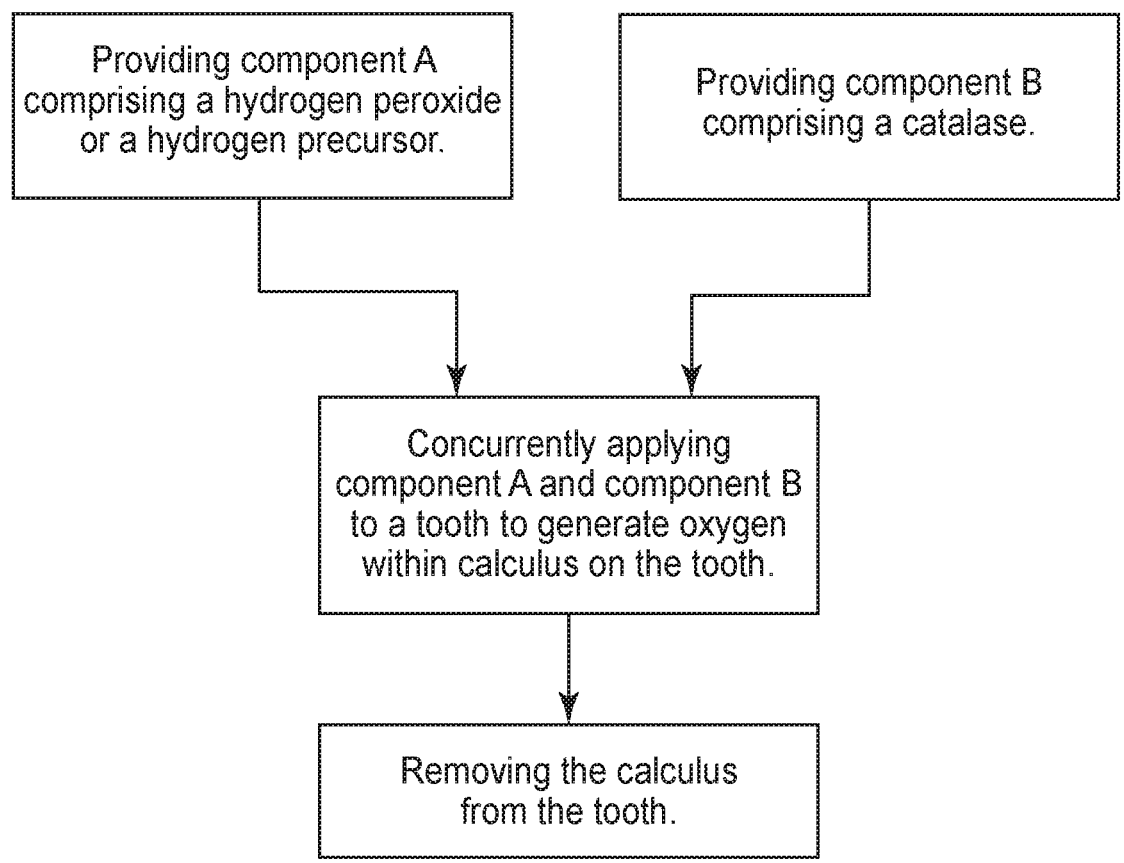
FIG. 1 is a block diagram illustrating the steps of present disclosure for removing calculus from a tooth according to one embodiment of the present disclosure.

Before any embodiments of the present disclosure are explained in detail, it is understood that the invention is not limited in its application to the details of use, construction, and the arrangement of components set forth in the following description. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

Dental calculus (also referred to as dental tartar) is defined as mineralized dental biofilm filled with crystals of various calcium phosphates or dental plaque that has partially or completely calcified. It may be caused by the continual accumulation of minerals from fluids in the oral environment on plaque on the teeth. Dental calculus is a common oral condition afflicting humans and a variety of animal species and the presence of dental calculus may lead to periodontal diseases. The existing methods of removing dental calculus, which rely upon mechanical means such as scaling, are time consuming and laborious for dental professionals, and can be a painful and unpleasant experience for patients.

The present disclosure generally relates to methods and kits of removing calculus from a tooth. Generally, the method can include providing a component A comprising a hydrogen peroxide or a hydrogen peroxide precursor; providing a component B comprising a catalase; applying the component A and the component B to the tooth, thereby generating oxygen to the tooth, thereby generating oxygen; and removing at least a part of the calculus from the tooth. In a preferred embodiment, component A and component B are each independently a liquid or a gel; and at least one of the component A and the component B has a viscosity of less than 26 Pa·s at a shear rate of 1/s at 25° C. In particular, surprisingly there is narrow range of catalase and hydrogen peroxide gel viscosities that eases calculus removal when both gels are applied concurrently, as discussed in further detail below and illustrated by the Examples.

Typically, the removal of dental calculus is challenging due to the generally strong adhesion of the calculus to the tooth surfaces, and the similar inorganic composition of the calculus and tooth tissues. However, by creating oxygen bubbles on the surface of the dental calculus on the tooth, or within the pores of the calculus on the tooth, with the method of the present invention, this physically helps break up the calculus to make it easier to remove from the tooth. The method of the present disclosure can, for example provide an easier removal of dental calculus. In addition, the method of the present disclosure can reduce the time of calculus removal. For example, after the application of the component A and component B, removing the calculus is easier and quicker. Thus, the method of the present disclosure can enable improved procedural efficiency, helping to reduce the amount of time dedicated to the dental prophylaxis procedure of calculus removal. This will increase the patient comfort during the calculus removal process, create opportunities for more patients, additional time for other procedures and increased rest periods for the dental professional, reducing their muscular and repetitive movement ailments, such as carpal tunnel syndrome).

In some embodiments, the component A can include hydrogen peroxide. The hydrogen peroxide can be generated by a peroxide generating enzyme in combination with the corresponding substrate, e.g., glucose oxidase and Superoxide Dismutase (SOD). For example, glucose oxidase can catalyze the oxidation of glucose to hydrogen peroxide. In some embodiments, the hydrogen peroxide may be in a form of a hydrogen peroxide adduct, such as carbamide peroxide, percarbonate salts or acids and poyvinylpyrrolidone (PVP) peroxide and combinations thereof. Suitable percarbonate salts or acids can include, but are not limited to percarbonic acid, sodium percarbonate, potassium percarbonate, magnesium percarbonate, calcium percarbonate, zinc percarbonate.

In some embodiments, the component A can include a hydrogen peroxide precursor, such as perborate salts or acids, metal peroxides, organic peroxide, inorganic peroxyacids or salts and combinations thereof. Suitable perborate salts or acids can include, but are not limited to perboric acid, sodium perborate, potassium perborate, magnesium perborate, calcium perborate, and zinc perborate. Suitable metal peroxides can include, but are not limited to calcium peroxide and magnesium peroxide. Suitable organic peroxides can include, but are not limited to peroxycarboxylic acids, such as peracetic acid or salts thereof, permalonic acid or salts thereof, pertartaric acid or salts thereof and percitric acid or salts thereof. In some embodiments, the organic peroxide can be a peracetate salt or acid. Suitable inorganic peroxyacids or salts can include, but are not limited to peroxymonosulfuric acid, peroxyphosphoric acid and a potassium salt of a sulfuric peroxyacid.

In some embodiments, the component A can include at least about 0.003 M hydrogen peroxide. In some of these embodiments, the component A can include from about 0.03 M to about 12 M hydrogen peroxide. In some of these embodiments, the component A can include from about 0.1 M to about 3 M hydrogen peroxide. In some embodiments, the component A can include hydrogen peroxide in an amount of about 0.01 wt %, about 0.1 wt %, about 1 wt %, about 5 wt %, about 10 wt %, about 30 wt %, about 35 wt %, or a range between and including any two of these values. In other embodiments, the component A can comprise a hydrogen peroxide precursor or hydrogen peroxide adduct capable of producing a similar concentration of hydrogen peroxide, for example, at least about 0.003 M hydrogen peroxide. For instance, a 15 wt % carbamide peroxide solution can produce a solution which includes about 5 wt % hydrogen peroxide.

In some embodiments, the component B can include a peroxidase. In some embodiments, the component B can include a catalase. Catalases can be found in a wide variety of eukaryotic and prokaryotic organisms including, but not limited to *Agrobacterium tumefaciens, Aliivibrio salmonicida, Anopheles gambiae, Aspergillus nidulans,* and *Aspergillus niger*. Suitable catalases that can be used in the present disclosure are well known in the art and can include those described in International Publication No. WO2012/072777. For example, suitable catalases can include catalase derived/isolated from bovine liver, *Aspergillus niger* and *Micrococcus lysodeikticus*. In some embodiments, catalase can be in an unisolated form, such as a part of or whole eukaryotic and prokaryotic organism. Catalases can catalyze the disproportionation of two molecules of hydrogen peroxide into two molecules water and one molecule oxygen.

In some embodiments, the component B can include greater than about 3 units/mL of catalase. In some embodiments, the component B can include greater than about 17 units/mL of catalase. As used herein, one unit catalase will decompose 1.0 μmole of hydrogen peroxide per minute at pH 7.0 at 25° C., while the hydrogen peroxide concentration falls from 10.3 to 9.2 mM, measured by the rate of decrease of $A_{240}$. In some of these embodiments, the component B can include catalase in an amount of about 30 units/mL, about 300 units/mL, about 3,000 units/mL, about 5,500 units/mL, about 30,000 units/mL, about 300,000 units/mL, or a range between and including any two of these values, for example from about 30 units/mL to about 3,000 units/mL. In some embodiments, component B can include from about 1,000 units/mL to about 20,000 units/mL catalase.

In some embodiments, after the component B is applied to the tooth surface, the concentration of catalase inside the oral cavity increases by at least about 5 units/mL saliva, about 10 units/mL saliva, about 20 units/mL saliva, about 30 units/mL saliva, about 100 units/mL saliva, about 300 units/mL saliva, about 3,000 units/mL saliva, about 5,500 units/mL saliva about 30,000 units/mL saliva, about 30,000 units/mL saliva or a range between and including any two of these values, above the natural concentration of catalase present inside the oral cavity prior to application of the component B.

One embodiment of the present method of the invention is illustrated in FIG. 1. A component A comprising a hydrogen peroxide or a hydrogen precursor, as described above, is provided. A component B comprising a catalase, as described above, is also provided. Then, both component A and component B are applied concurrently to a tooth to generate oxygen within the calculus of the tooth, as described above. For instance, component A or component B may be applied at about the same time, jointly, or even applied simultaneously to the tooth. Typically, when component A and component B are applied concurrently, a user observes the oxygen bubbles generated along the surface of the calculus (i.e., such bubbles are observable to the naked human eye).

After component A and component B are applied concurrently to the surface of the calculus of the tooth and the desired oxygen is produced within the calculus to help break up the calculus, the calculus is removed from the tooth by a mechanical methods or process, such as by hand or ultrasonic scaling or by prophy powder or tooth paste. One example of suitable a dental hand scaler is commercially available as a universal (i.e., Columbia) curette from either OSUNG MND CO., LTD. (Korea) or Hu-Friedy (Netherlands). One example of a dental ultrasonic scaler is commercially available as SIROSONIC ultrasonic scaler, C-series from Sirona Dental (US).

Figure 2:
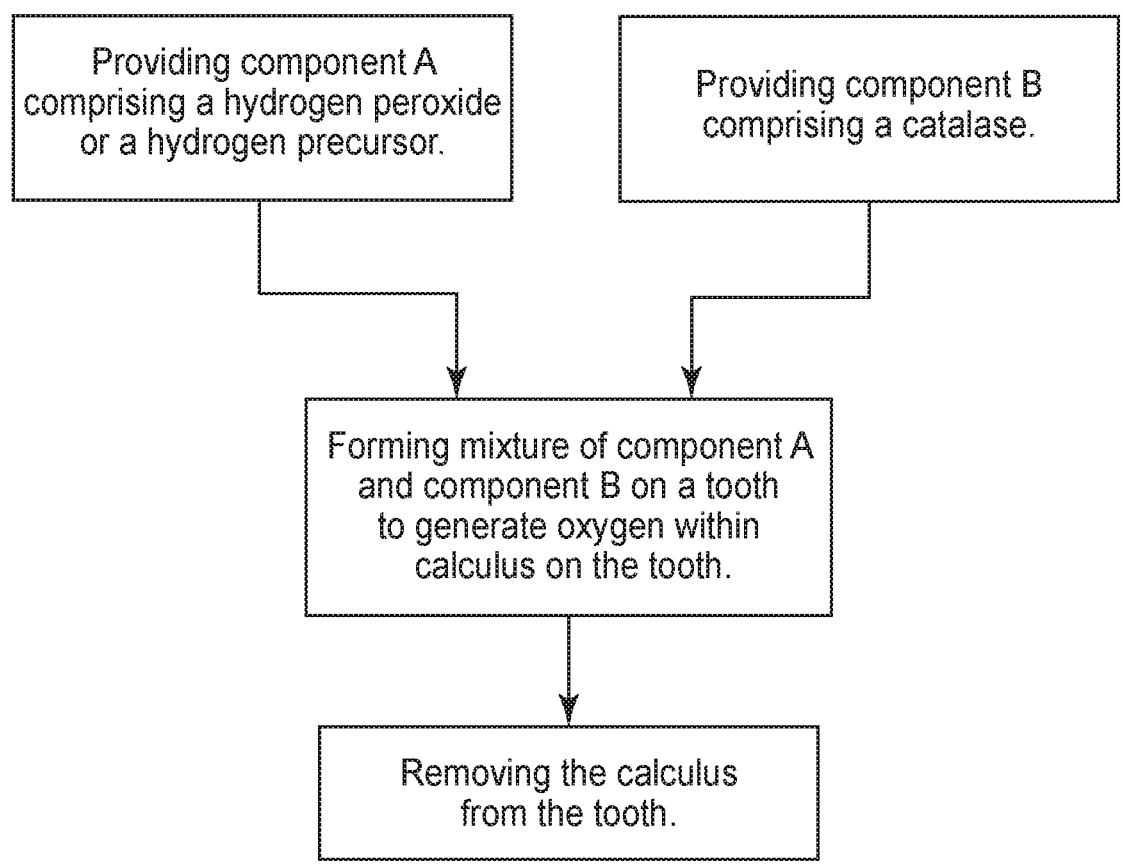
FIG. 2 is a block diagram illustrating the steps of present disclosure for removing calculus from a tooth according to another embodiment of the present disclosure.

In a more specific embodiment, as illustrated in FIG. 2, component A and component B may form a mixture on the tooth as they are being concurrently applied. For example, component A and component B may be applied to the tooth surface by a double barrel syringe, where one nozzle opening delivers component A and the other nozzle opening delivers component B to the surface of the tooth. The nozzle openings could be arranged such that component A and component B are applied on the same general area of the calculus, and are then necessarily mixed and intermingled to form a mixture and produce the desired oxygen generation within the calculus. Alternatively, the nozzle openings could be arranged such that at least certain portions of component A and component B overlap and are then necessarily mixed and intermingled to form a mixture and produce the desired oxygen generation within the calculus. As yet another alternative, if the component A and component B do not overlap, when applied to the tooth surface, they may be mixed with the nozzle of the syringe or by other instruments such as a scaler, to form the mixture of component A and component B on the tooth surface, and thereby produce the desired oxygen generation within the calculus. Typically, when component A and component B are mixed, a user observes the oxygen bubbles generated along the surface of the calculus. Regardless of how the mixture is exactly formed on the tooth surface, the calculus is thereafter removed from the tooth by a mechanical means or process, hand or ultrasonic scaling, as described above.

Figure 3:
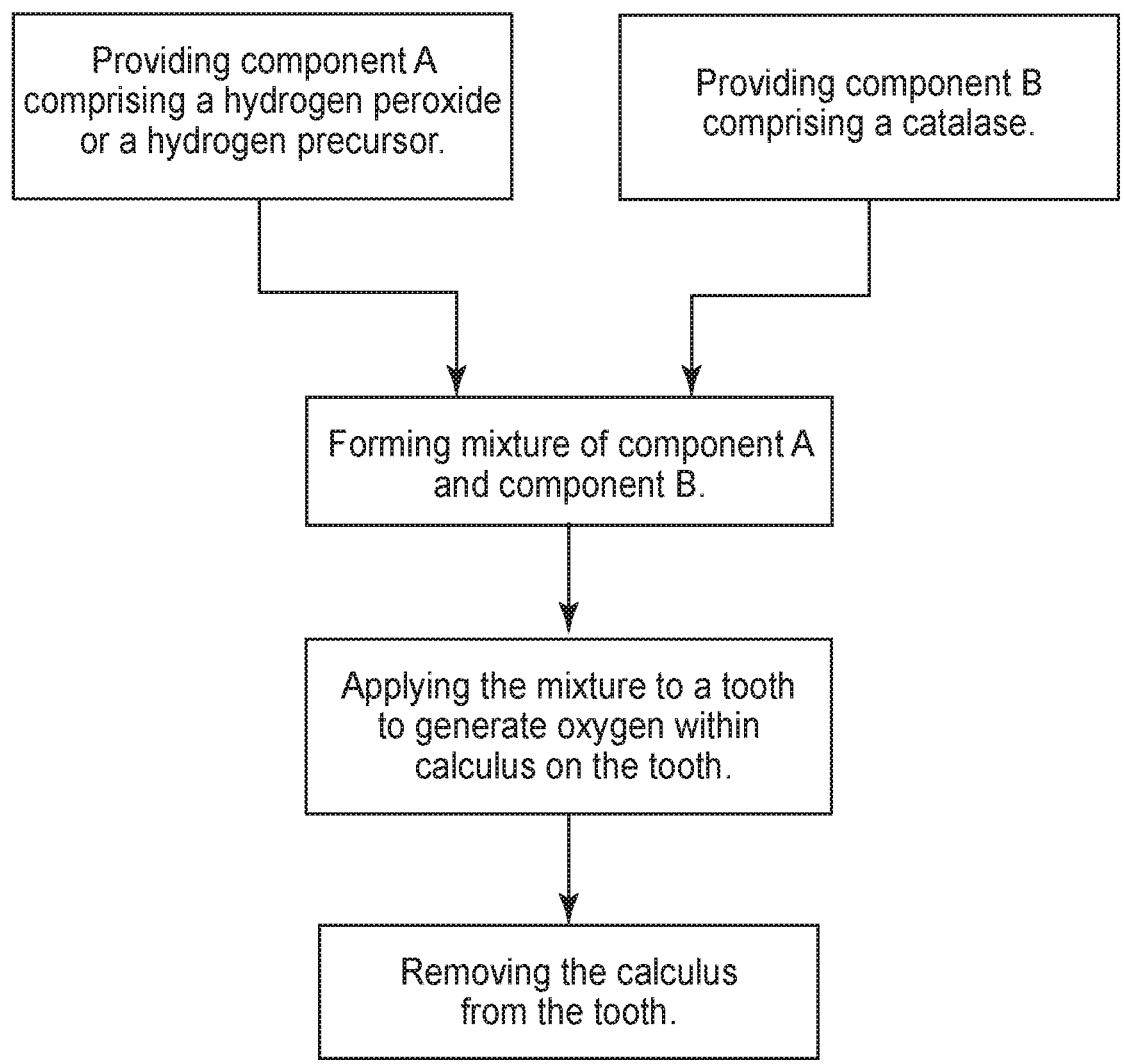
FIG. 3 is a block diagram illustrating the steps of present disclosure for removing calculus from a tooth according to yet another embodiment of the present disclosure.

In another specific embodiment, as illustrated in FIG. 3, the mixture of component A and component B may be formed just prior to application of such mixture to the surface of the tooth to generate the desired production of oxygen within the calculus on the tooth. For example, component A and component B may be applied to the tooth surface by a double barrel syringe having a static mixer. Each barrel delivers a component and the static mixer mixes component A and component B just prior to exiting the nozzle of the static mixer, which delivers the mixture to the surface of the tooth. While the component A and component B are mixing within the static mixer, it can begin to produce the desired oxygen generation and is then thereafter applied to the calculus on the tooth. Typically, when the mixture of component A and component B are applied to the calculus, a user observes the oxygen bubbles generated along the surface of the calculus. One example of a suitable dual barrel static mixer syringe is disclosed in PCT Published Patent Application 2015/073246 entitled "A Cartridge, A Piston and A Syringe Comprising the Cartridge and the Piston," which is hereby incorporated by reference. Another suitable dual barrel static mixer syringe is commercially available from Sulzer Mixpac (USA).

In one embodiment, the mixture of component A and component B are applied concurrently for at least 5-10 seconds on an individual tooth before the calculus is removed by mechanical methods. In another embodiment, the mixture of component A and the component B is applied concurrently to the tooth for a time period less than about 1 hour prior to the removing step. In yet another embodiment, the removing step occurs within 24 hours after the applying step. In yet another embodiment, the applying step and the removing step are all completed in less than 24 hours. In another embodiment, the applying step and the removing step are completed in less than 1 hour, ideally less than 20-35 minutes for this process to be completed for the typical dental patient. However, the length of time to complete the method of the present invention can and will vary based any number of factors, including, but not limited to, the amount, area, tenacity, depth of calculus on the patient's teeth, and the total number and location (e.g. posterior vs. anterior) of teeth being treated. It is expected that the method will be performed by a dental professional, such as dental hygienist or dentist, and the method would be customized for the individual patient. For example, component A and component B may be applied concurrently to a patient's individual tooth having calculus and thereafter the calculus is removed from that specific tooth. As another example, component A and component B may be mixed in a static mixer and then applied to the entire arch of the patient's teeth.

In some embodiments, the component A or component B is applied concurrently for a period less than about 1 hour, less than about 30 minutes, less than about 10 minutes, less than about 5 minutes, less than about 2 minutes, or less than about 1 minute. In some of these embodiments, the component A or component B is concurrently applied for about 10 minutes, about 5 minutes, about 2 minutes, about 1 minute, about 30 seconds, about 15 seconds or a range between and including any two of these values. In some embodiments, both the component A and the component B are each applied concurrently for a period less than about 1 hour, less than about 30 minutes, less than about 10 minutes, less than about 5 minutes, less than about 2 minutes, or less than about 1 minute.

Regardless of which embodiment of the methods illustrated in FIGS. 1-3 and discussed above are used, if component A includes a hydrogen peroxide adduct, the hydrogen peroxide dissociates from the adduct in the environment within the oral cavity to produce hydrogen peroxide. In some embodiments, hydrogen peroxide in the presence of peroxidase, e.g., catalase can cause release of oxygen, thereby loosening the calculus from the tooth. The generated oxygen can, for example weaken the adhesion between the calculus and tooth surface so that the calculus can be removed easily after relatively short exposure times to the mixture of Component A and Component B. In some embodiments, the generated oxygen can soften and/or loosen the calculus so that the removal of the calculus, for example, by hand scaling is much easier. For instance, the calculus can be removed in a shorter time or with a less force. The catalase concentration typically present in human saliva or oral cavity is not sufficient to provide these effects.

After the component A and the component B are concurrently applied, at least a part of the calculus can be removed from the tooth by any suitable mechanical means, e.g., scaling (such as using a dental scaler), brushing, swabbing, wiping, ultrasonic, air polishing or jetted water. In some embodiments, the part of the calculus may be removed by mechanical means other than tooth brushing, for example by a dental scaler. In some embodiments, removing step occurs within 1 day, 12 hours, 6 hours, 3 hours, 1 hour, 30 minutes, 10 minutes, 5 minutes, 2 minutes, 1 minute, 30 seconds, or 15 seconds after the applying steps. In some embodiments, removing step lasts for a period less than about 10 minutes, less than about 5 minutes, less than about 2 minutes, or less than about 1 minute. In other embodiments, removing step lasts about 10 minutes, about 5 minutes, about 2 minutes, about 1 minute, about 30 seconds, or a range between and including any two of these values. Thus, the method of the present disclosure can, for example, provide an easier and/or quicker removal of the calculus. In some embodiments, the applying steps and removing step are all completed in less than about 1 day, about 12 hours, about 6 hours, about 3 hours, about 1 hour, about 30 minutes, about 10 minutes, about 5 minutes, about 2 minutes, or about 1 minute. Typically, the method of the present invention is completed in the course of a single dental visit.

Either component A or component B can be (independently) in any form liquid or gel form suitable for oral cavity delivery, such as in the form of aqueous solutions (e.g., a rinse), a paste, or a gel. For example, component A and component B can be concurrently applied both as rinses. In some embodiments, component A can be concurrently applied as a gel and component B can be applied as a rinse. In other embodiments, component A and component B can be concurrently applied both as gels.

As mentioned above, preferably at least component A or the component B has a viscosity of less than 26 Pa·s at a shear rate of 1/s at 25° C. In an alternative embodiment, the component A and the component B each have a viscosity of less than 26 Pa·s at a shear rate of 1/s at 25° C. In other embodiments, the component A and the component B each have a viscosity of less than 16 Pa·s at a shear rate of 1/s at 25° C. In other embodiments, at least one of the component A and the component B has a viscosity of greater than 2 Pa·s at a shear rate of 1/s at 25° C. In some embodiments, the component A and the component B each have a viscosity of greater than 2 Pa·s at a shear rate of 1/s at 25° C. In some embodiments, the viscosities of components A and B are similar, e.g. the viscosities can differ by less than 5, 4, 3 or 2 Pa·s. This may be desirable where components A and B are delivered as a mixture using a static mixer to ensure the effective missing of the components.

In some embodiments, methods of the present disclosure include relatively short exposure times of the combination of component A and component B, such that no noticeable bleaching or tooth whitening is observed by the naked eye when the method is completed, e.g., in a single instance, and in some cases, over multiple instances.

In some embodiments, additives can be applied to the tooth surface. In some of these embodiments, additives can be applied with the component A and/or the component B. The additives used in the method can include, but are not limited to, antiseptics and preservatives, antibiotics, flavoring materials, surfactants, abrasives, thickeners and binders, propellants, carriers, tartar control agents, calcium sequestrants, fluoride salts, and dyes.

Suitable antiseptics and preservatives can include, but are not limited to, chlorhexidine and salts thereof, polyhexamethylene biguanide, octenidine, quaternary ammonium salts and polymers thereof, organic acids, chelating agents for example a calcium chelating agent (e.g., Ethylenediaminetetraacetic acid (EDTA)), essential oils, and parabens. Examples of antiseptics and preservatives can include those described in U.S. Pat. No. 8,647,608. Non-limiting examples of antibiotics can include penicillin, tetracycline, minocycline, and the like. Examples of antibiotics can also include those described in U.S. Pat. No. 6,685,921. Examples of flavoring materials can include artificial sweeteners, plant oils, and synthetic flavors. Examples of abrasives can include silica particles, synthetic inorganic particles, and synthetic or plant derived organic particles. Suitable surfactants can include those described in U.S. Publication No. 2006/0051385. Examples of such surfactants include cationic surfactants, zwitterionic surfactants, non-ionic surfactants and anionic surfactants.

Examples of thickeners can include glycerol, silica, polysaccharides (including cellulose-based polymers and derivatives), plant gums (e.g. guar and xanthan gum), petroleum derived materials such as petrolatum, polyethylene glycols, polyvinyl pyrrolidone and co-polymers thereof, polylactic acids, long chain fatty acid alcohols, acrylate polymers, and polyacrylic acids gelatin, or combinations thereof. One example of a suitable polyacrylic acid is a cross-linked polyacrylic acid commercially available under the trade designation CARBOPOL (e.g. Carbopol 971) from Lubrizol Corporations located in Wickliffe, Ohio). The thickeners may include one or more inorganic or a natural or synthetic thickeners or gelling agents. Any orally acceptable thickener can be used. Suitable thickeners or gelling agents include amorphous silica (e.g., as available from Huber Corporation under the trade designation ZEODENT 165), fumed silica, precipitated silica, colloidal silica, natural and synthetic gums and colloids, poloxamers, carbomers, also known as carboxyvinyl polymers, carrageenan, Irish moss, iota-carrageenan, cellulosic polymers such as hydroxyethylcellulose, carboxymethylcellulose (carmellose, cellulose gum) and salts thereof, e.g., carmellose sodium, natural gums such as karaya, xanthan, gum Arabic, gum tragacanth, polyvinylpyrrolidone, agar, colloidal magnesium aluminum silicate, and combinations thereof. The thickener or gelling agent can be independently dissolved, dispersed, suspended, or emulsified in component A, component B, or in both. In some embodiments, the thickener or gelling agent can be dissolved, dispersed, suspended, or emulsified in the carrier.

Suitable carriers can include those described in U.S. Pat. No. 8,647,608. Carriers can include any alcohols suitable for use in a subject's oral cavity, including ethanol and isopropanol and glycerol.

In various embodiments, at least one of the component A and the component B includes a carrier. The carrier, if present, can include a liquid, a gel, or both. In some embodiments, the carrier can be a liquid at about room temperature. In some embodiments, the carrier can be a liquid at about the temperature of the oral cavity of a human, i.e., at about 37° C. It is understood that a plurality of carriers can be used. Examples of liquid carriers include, but are not limited to, water, glycerin, propylene glycol, polyalkylene glycols (e.g., polyethylene glycol, polypropylene glycol, etc.), polyglycerol, and combinations thereof.

Further examples of suitable carriers include those described in U.S. Pat. No. 6,669,929 (Boyd et al.), U.S. Pat. No. 6,379,654 (Gebreselassie et al.), and U.S. Pat. No. 4,894,220 (Nabi et al.), each of which is incorporated herein by reference in its entirety.

Suitable dyes include those described in U.S. Pat. No. 8,647,608. Examples of tartar control agents include those described in U.S. Pat. No. 6,685,921. Anti-tartar agents known for use in dental care products can include, but are not limited to phosphate. Phosphates can include pyrophosphates, polyphosphates, polyphosphonates and mixtures thereof. Pyrophosphate salts can include the dialkali metal pyrophosphate salts, tetra-alkali metal pyrophosphate salts and mixtures thereof. Examples of fluoride salts can include those described in U.S. Pat. Nos. 6,685,921, 3,535,421 and 3,678,154.

The kits of removing calculus from a tooth of the present disclosure can include a component A comprising a hydrogen peroxide or a precursor thereto and a component B comprising a catalase. The component A of the kit is applied to the tooth before or after the component B of the kit is applied to the tooth.

The following embodiments are intended to be illustrative of the present disclosure and not limiting.

Embodiments

Embodiment 1 is a method of removing calculus from a tooth comprising:
  providing a component A, wherein the component A comprises a hydrogen peroxide or a precursor thereto;
  providing a component B, wherein the component B comprises a catalase;
  applying the component A and the component B to the tooth, thereby generating oxygen; and
  removing at least a part of the calculus from the tooth;
  wherein component A and component B are each independently a liquid or a gel; and
  wherein at least one of the component A and the component B has a viscosity of less than 26 Pa·s at a shear rate of 1/s at 25° C.

Embodiment 2 is the method of embodiment 1, wherein in the applying step, component A and component B are applied concurrently to the tooth.

Embodiment 3 is the method of embodiments 1 to 2, wherein in the applying step, component A and component B form a mixture on the tooth.

Embodiment 4 is the method of embodiments 1 to 2, wherein prior to the applying step, component A and component B are mixed to form a mixture, and wherein in the applying step, the mixture is applied to the tooth.

Embodiment 5 is the method of embodiments 1 to 4, wherein in the applying step, the mixture of component A and the component B is applied to the tooth for a time period less than about 1 hour prior to the removing step.

Embodiment 6 is the method of embodiments 1 to 5, wherein in the applying step, component A and the component B are applied to the tooth for a time period less than 1 hour prior to the removing step.

Embodiment 7 is the method of embodiments 1 to 6, wherein the removing step occurs within 24 hours after the applying step.

Embodiment 8 is the method of embodiments 1 to 7, wherein the applying step and the removing step are all completed in less than 24 hours.

Embodiment 9 is the method of embodiments 1 to 8, wherein the applying step and the removing step are completed in less than 1 hour.

Embodiment 10 is the method of embodiments 1 to 9, wherein the component A comprises at least about 0.003 M hydrogen peroxide.

Embodiment 11 is the method of embodiments 1 to 10, wherein the component A comprises from about 0.03 M to about 12 M hydrogen peroxide.

Embodiment 12 is the method of embodiments 1 to 11, wherein the component A comprises from about 0.1 M to about 3 M hydrogen peroxide.

Embodiment 13 is the method of embodiments 1 to 12, wherein the component B comprises greater than about 3 units/mL of catalase.

Embodiment 14 is the method of embodiments 1 to 13, wherein the component B comprises from about 30 units/mL to about 300,000 units/mL catalase.

Embodiment 15 is the method of embodiments 1 to 14, wherein the component B comprises from about 1,000 units/mL to about 20,000 units/mL catalase.

Embodiment 16 is the method of embodiments 1 to 15, wherein the component A and the component B each have a viscosity of less than 26 Pa·s at a shear rate of 1/s at 25° C.

Embodiment 17 is the method of embodiments 1 to 16, wherein the component A and the component B each have a viscosity of less than 16 Pa·s at a shear rate of 1/s at 25° C.

Embodiment 18 is the method of embodiments 1 to 17, wherein at least one of the component A and the component B has a viscosity of greater than 2 Pa·s at a shear rate of 1/s at 25° C.

Embodiment 19 is the method of embodiments 1 to 18, wherein the component A and the component B each have a viscosity of greater than 2 Pa·s at a shear rate of 1/s at 25° C.

Embodiment 20 is the method of embodiments 1 to 19, wherein the hydrogen peroxide is a hydrogen peroxide adduct.

Embodiment 21 is the method of embodiments 1 to 20, wherein the hydrogen peroxide adduct is selected from the group consisting of carbamide peroxide, percarbonate salts or acids, polyvinylpyrrolidone (PVP) peroxide and combinations thereof.

Embodiment 22 is the method of embodiments 1 to 21, wherein the hydrogen peroxide precursor is selected from the group consisting of perborate salts or acids, metal peroxides, organic peroxide, inorganic peroxyacids or salts and combinations thereof.

Embodiment 23 is the method of embodiments 1 to 22, wherein the precursor is an organic peroxide, and wherein the organic peroxide is a peracetate salt or acid.

Embodiment 24 is the method of embodiments 1 to 23, wherein the hydrogen peroxide is generated by a peroxide generating enzyme.

Embodiment 25 is the method of embodiments 1 to 24, wherein at least one of the component A and the component B comprises a carrier.

Embodiment 26 is the method of embodiment 25, wherein the carrier comprises water, glycerol, a polyethylene glycol, a polyglycerol, or combinations thereof.

Embodiment 27 is the method of embodiments 1 to 26, wherein at least one of the component A and the component B comprises a thickener.

Embodiment 28 is the method of embodiment 27, wherein the thickener is polyacrylic acid, gelatin, a polysaccharide, silica, or combinations thereof.

Embodiment 29 is the method of embodiments 1 to 27, wherein the removing step comprises removing by mechanical means.

Embodiment 30 is the method of embodiments 1 to 29, wherein the removing step at comprises removing by mechanical means other than tooth brushing.

Embodiment 31 is the method of embodiments 1 to 30, wherein the removing step comprises removing at least a part of the calculus from the tooth with a dental scaler.

Embodiment 32 is the method of embodiments 1 to 31, wherein no tooth whitening is observable to the naked human eye, after the applying step or removing step.

Embodiment 33 is a kit of parts for removing calculus from a tooth comprising:
- a component A comprising a hydrogen peroxide or a precursor thereto; and
- a component B comprising a catalase;
- wherein component A and component B are each independently a liquid or a gel; and
- wherein at least one of component A and component B has a viscosity of less than 26 Pa·s at a shear rate of 1/s at 25° C.

EXAMPLES

The following examples are given to illustrate, but not limit, the scope of this invention. As used herein, all parts and percentages are by weight unless otherwise specified. All commercial materials were used as obtained from the vendor. Unless otherwise specified, materials can be obtained from Sigma-Aldrich Corp. (St. Louis, Mo.).

Materials & Methods

*Aspergillus niger* catalase enzyme with an activity of 967,500 units (U) per gram (g) was obtained from American Laboratories (Omaha, Nebr.). One unit of this enzyme decomposes 1.0 µmol of hydrogen peroxide ($H_2O_2$) per minute at pH 7.0 at 25° C. As used herein, one unit catalase will decompose 1.0 µmole of hydrogen peroxide per minute at pH 7.0 at 25° C., while the hydrogen peroxide concentration falls from 10.3 to 9.2 mM, measured by the rate of decrease of $A_{240}$. Carbopol 971P NF, a crosslinked polyacrylic acid polymer, was obtained from Lubrizol Corporation (Wickliffe, Ohio). $H_2O_2$ was obtained in the form of a 30 wt. % aqueous solution from Avantor Performance Materials (Center Valley, Pa.). Diluted aqueous hydrogen peroxide solutions were prepared using deionized water. The molarity of the aqueous hydrogen peroxide solutions at room temperature (~23° C.) was calculated from the weight percent and approximate density of the solutions (densities were calculated at 25° C. using Equation (3) in Easton, M. F., Mitchell, A. G., Wynne-Jones, W. F. K., "The Behaviour of Mixtures of Hydrogen Peroxide and Water. Part I. Determination of the Densities of Mixtures of Hydrogen Peroxide and Water", Trans. Faraday Soc., 48, 796 (1952)).

Preparation of Test Formulations (Hydrogen Peroxide and Catalase Components)

Hydrogen peroxide containing gels with varying viscosities, each having 3.0 wt. % (approximately 0.88M) hydrogen peroxide, were prepared by diluting concentrated (30 wt. %) aqueous hydrogen peroxide with deionized water, adding sufficient Carbopol 971P NF (Lubrizol Corporation, Wickliffe, Ohio, USA) to arrive at a hydrogen peroxide containing gel with the desired amount of Carbopol 971P NF (i.e., gels containing 3 wt. % hydrogen peroxide and 0.5 wt. %, 1.0 wt. % or 2.0 wt. % Carbopol 971P NF), and then adjusting the pH to 7.4 by adding a small volume 40 wt. % aqueous potassium hydroxide. A low viscosity solution containing 3 wt. % hydrogen peroxide was prepared by dilution of 30 wt. % hydrogen peroxide with deionized water.

A. Niger catalase containing gels with varying viscosities, each having 5,000 U catalase per gram of gel (approximately 5,500 U catalase per mL of gel), were prepared as follows. The catalase was dissolved into phosphate buffered saline, and sufficient glycerol was added such that the eventual gel would include 35 wt. % glycerol. Sufficient Carbopol 971P NF was added to arrive at a catalase containing gel with the desired amount of Carbopol 971P NF (i.e., gels containing 35 wt. % glycerol and 5,000 U catalase per gram of gel, and 0.5 wt. %, 1.0 wt. %, or 2.0 wt. % Carbopol 971P NF). The pH was adjusted to 7.4 by adding a small volume of 40 wt. % aqueous potassium hydroxide. A low viscosity solution containing 3,000 U of A. niger catalase per gram of solution (approximately 3,300 U per mL of solution) was made by dissolving the appropriate amount of catalase into phosphate buffered saline.

Viscosity Measurements

Viscosities were measured using a flat, 20 mm stainless steel plate on an ARG2 rheometer (TA Instruments, New Castle, Del.) at a shear rate of about 1/s using a 1 mm gap at 25° C. Viscosity measurements for the components are reported in Pa·s.

Evaluation of Test Formulations Generally

Extracted human teeth containing multiple regions with calculus deposits (available from various suppliers such as enretec GmbH, Velten, Germany) were obtained and stored in 0.5-1.0 wt. % aqueous chloramine-T solution prior to use. To prepare the extracted teeth for calculus removal testing, the teeth were rinsed with deionized water. Hand scaling of calculus deposits as described in the following examples was performed using a universal (i.e., Columbia) curette commercially available from either OSUNG MND CO., LTD. (Korea) or Hu-Friedy (Netherlands).

Calculus-covered regions on extracted human teeth were treated with either water (control) or test formulations. The effectiveness of the treatment was determined by comparing the ease of calculus removal by hand scaling half of each calculus-covered region after application of water onto calculus versus ease of hand scaling after application of the formulation on the second half of each calculus-covered region on the same tooth. The formulation was scored as efficacious (+) if the formulation improved the ease of removing the calculus with a hand scaler. The formulation was scored as not efficacious (−) if there was no observation of improved ease of removal of calculus.

Example 1 (EX-1)

Component A: Hydrogen peroxide containing gel with 3 wt. % hydrogen peroxide and 0.5 wt. % Carbopol 971P NF, pH adjusted to 7.4, with a viscosity of 2.05 Pa·s at a shear rate of 1/s at 25° C.

Component B: Catalase containing gel with 5,000 U A. niger catalase per gram of gel (5,500 U/mL of gel), 35 wt. % glycerol, and 0.5 wt. % Carbopol 971P NF, pH adjusted to 7.4, with a viscosity of 3.14 Pa·s at a shear rate of 1/s at 25° C.

Three separate teeth were hand scaled following the application of either water or the treatment formulation to calculus-covered regions on each tooth. The effectiveness of the treatment was determined by comparing the ease of calculus removal by hand scaling half of each calculus-covered region after application of water onto calculus versus ease of hand scaling after application of the treatment formulation on the second half of each calculus-covered region on the same tooth. Component A and Component B were loaded into a dual barrel syringe (1:1 volume ratio) equipped with a static mixing tip. The components were applied to the calculus-covered tooth surface as a mixture in a sufficient amount to cover the calculus deposit, by extruding the components through the static mixer using hand pressure on the plunger of the dual barrel syringe. After application of the mixture, the operator waited 5 to 20 seconds and then began scaling. In two out of three teeth, an improvement in the ease of removal of calculus by the operator was observed.

Example 2 (EX-2)

Component A: Hydrogen peroxide containing gel with 3 wt. % hydrogen peroxide and 1.0 wt. % Carbopol 971P NF, pH adjusted to 7.4, with a viscosity of 11.53 Pa·s at a shear rate of 1/s at 25° C.

Component B: Catalase containing gel with 5,000 U A. niger catalase per gram of gel (5,500 U/mL of gel), 35 wt. % glycerol, and 1.0 wt. % Carbopol 971P NF, pH adjusted to 7.4, with a viscosity of 15.24 Pa·s at a shear rate of 1/s at 25° C.

Three separate teeth were hand scaled following the application of either water or the treatment formulation to calculus-covered regions on each tooth. The effectiveness of the treatment was determined by comparing the ease of calculus removal by hand scaling half of each calculus-covered region after application of water onto calculus versus ease of hand scaling after application of the treatment formulation on the second half of each calculus-covered region on the same tooth. Component A and Component B were loaded into a dual barrel syringe (1:1 volume ratio) equipped with a static mixing tip. The components were applied to the calculus-covered tooth surface as a mixture in a sufficient amount to cover the calculus deposit, by extruding the components through the static mixer using hand pressure on the plunger of the dual barrel syringe. After application of the mixture, the operator waited 5 to 20 seconds and then began scaling. In two out of three teeth, an improvement in the ease of removal of calculus by the operator was observed.

Example 3 (EX-3)

Component A: 3 wt. % hydrogen peroxide solution with a viscosity similar to water, (approximately 0.001 Pa·s).

Component B: Catalase containing phosphate buffered saline solution with 3,000 U A. niger catalase per gram of solution (3,300 U/mL of solution), with a viscosity similar to water.

Four separate calculus-covered regions on at total of three separate teeth (i.e., one of the three teeth contained two calculus-covered regions on the same tooth) were hand scaled following the application of either water or the treatment formulation to calculus-covered regions on each tooth. The effectiveness of the treatment was determined by comparing the ease of calculus removal by hand scaling half of each calculus-covered region after application of water onto calculus versus ease of hand scaling after application of the treatment formulation on the second half of each calculus-covered region on the same tooth. Component A and Component B were loaded into a dual barrel syringe (1:1 volume ratio) equipped with a static mixing tip. The components were applied to the calculus-covered tooth surface as a mixture in a sufficient amount to cover the calculus deposit, by extruding the components through the static mixer using hand pressure on the plunger of the dual barrel syringe. After application of the mixture, the operator waited 5 to 20 seconds and then began scaling. In two out of four calculus-covered regions on at total of three teeth, an improvement in the ease of removal of calculus by the operator was observed.

Comparative Example 1 (CE-1)

Component A: Hydrogen peroxide containing gel with 3 wt. % hydrogen peroxide and 0.5 wt. % Carbopol 971P NF, pH adjusted to 7.4, with a viscosity of 2.05 Pa·s at a shear rate of 1/s at 25° C.
Component B: Dry *A. niger* catalase powder.
Three separate teeth were hand scaled following the application of either water or the treatment formulation to calculus-covered regions on each tooth. The effectiveness of the treatment was determined by comparing the ease of calculus removal by hand scaling after application of water in the first region of calculus versus ease of calculus removal after application of the treatment formulation on the second region of calculus on the same tooth. 1-2 mg of dry catalase powder (Component B) was applied to the tip of a cotton swab and then the swab was covered in Component A by rolling the tip of the catalase-loaded swab in Component A on a piece of weighing paper. After 20-30 seconds the swab was used to apply the mixture onto the calculus, in a sufficient amount to cover the calculus deposit. After application of the mixture, the operator waited 5 to 20 seconds and then began scaling. In three out of three teeth, no improvement in the ease of removal of calculus by the operator was observed.

Comparative Example 2 (CE-2)

Component A: Hydrogen peroxide containing gel with 3 wt. % hydrogen peroxide and 2.0 wt. % Carbopol 971P NF, pH adjusted to 7.4, with a viscosity of 26.22 Pa·s at a shear rate of 1/s at 25° C.

Component B: Catalase containing gel with 5,000 U *A. niger* catalase per gram of gel (5,500 U/mL of gel), 35 wt. % glycerol, and 2.0 wt. % Carbopol 971P NF, pH adjusted to 7.4, with a viscosity of 39.53 Pa·s at a shear rate of 1/s at 25° C.

Six separate calculus-covered regions on a total of three separate teeth were hand scaled following the application of either water or the treatment formulation to the calculus-covered regions on each tooth. The effectiveness of the treatment was determined by comparing the ease of calculus removal by hand scaling half of each calculus-covered region after application of water onto of calculus versus application of the treatment formulation on the second half of each calculus-covered region on the same tooth. Component A and Component B were loaded into a dual barrel syringe (1:1 volume ratio) equipped with a static mixing tip. The components were applied to the calculus-covered tooth surface as a mixture in a sufficient amount to cover the calculus deposit, by extruding the components through the static mixer using hand pressure on the plunger of the dual barrel syringe. After application of the gels, the operator waited 5 to 20 seconds and then began scaling. In six out of six calculus-covered regions on three teeth, no improvement in the ease of removal of calculus by the operator was observed.

As shown in Table 1, liquids and gels with viscosities below 26 Pa·s at a shear rate of 1/s at 25° C. eased the removal of dental calculus by hand scaling when delivered concurrently onto tooth surfaces.

TABLE 1

| Example | Component A Viscosity (Pa · s at a shear rate of 1/s at 25° C.) | Component B Viscosity (Pa · s at a shear rate of 1/s at 25° C.) | Tooth ID Numbers (calculus regions) | Total Number of Regions Tested | Ease of Removal Improvement Score (+ or −) for tested regions |
|---|---|---|---|---|---|
| EX-1 | 2.05 | 3.14 | 1 (one region), 2 (one region), 3 (one region) | 3 | 2 out of 3 were + |
| EX-2 | 11.53 | 15.24 | 4 (one region), 5 (one region), 6 (one region) | 3 | 2 out of 3 were + |
| EX-3 | Similar to water | Similar to water | 10 (one region), 11 (two regions), 12 (one region) | 4 | 2 out of 4 were + |
| CE-1 | 2.05 | N/A (dry powder) | 13 (one region), 14 (one region), 15 (one region) | 3 | 3 out of 3 were − |
| CE-2 | 26.22 | 39.53 | 7 (three regions), 8 (one region), 9 (two regions) | 6 | 6 out of 6 were − |

Example 4 (EX-4)

Component A: Hydrogen peroxide containing gel with 3 wt. % hydrogen peroxide and 0.5 wt. % Carbopol 971P NF, pH adjusted to 7.4, with a viscosity of 2.05 Pa·s at a shear rate of 1/s at 25° C.

Component B: Catalase containing gel with 5,000 U *A. niger* catalase per gram of gel (5,500 U/mL of gel), 35 wt. % glycerol, and 0.5 wt. % Carbopol 971P NF, pH adjusted to 7.4, with a viscosity of 3.14 Pa·s at a shear rate of 1/s at 25° C.

Experiment 1 is repeated, except that Component A and Component B are applied concurrently, but separately and without mixing, to a calculus-covered region of a single tooth. The application of Component A and Component B to the calculus-covered region may be performed by loading the components in to a dual barrel syringe (1:1 volume ratio) equipped with a tip that includes a septum which prevents the components from mixing in the syringe tip. After application, Component A and Component B (in the form of neighboring gel droplets on the calculus-covered region of the tooth) are mixed for several seconds at the calculus-covered region, using the syringe tip. After mixing, the operator waits 5 to 20 seconds and then begins scaling. An improvement in the ease of removal of calculus by the operator is expected (in comparison to using water).

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

The complete disclosures of the patents, patent documents, and publications cited herein are incorporated by reference in their entirety as if each were individually incorporated. For example, other various methods for calculus removal are disclosed in PCT Patent Application Serial Number PCT/US2015/063335, "Methods and Kits of Removing Calculus," filed on Dec. 2, 2015, which is hereby incorporated by reference.

What is claimed is:

1. A method of removing calculus from a tooth comprising:
providing a component A,
the component A comprising hydrogen peroxide or a hydrogen peroxide precursor;
providing a component B,
the component B comprises a catalase;
applying the component A and the component B to the tooth, thereby generating oxygen; and
removing at least a part of the calculus from the tooth,
wherein at least one of the component A and the component B is characterized by a viscosity of less than 26 Pa·s at a shear rate of 1/s at 25° C.

2. The method of claim 1, wherein in the applying step, component A and component B are applied concurrently to the tooth.

3. The method of claim 1, wherein prior to the applying step, component A and component B are mixed to form a mixture, and wherein in the applying step, the mixture is applied to the tooth.

4. The method of claim 1, wherein in the applying step, component A and the component B are applied to the tooth for a time period less than 1 hour prior to the removing step.

5. The method of claim 1, wherein the removing step occurs within 24 hours after the applying step.

6. The method of claim 1, wherein the applying step and the removing step are completed in less than 1 hour.

7. The method of claim 1, wherein the component A comprises at least about 0.003 M hydrogen peroxide.

8. The method of claim 1, wherein the component A comprises from about 0.03 M to about 12 M hydrogen peroxide.

9. The method of claim 1, wherein the component A comprises from about 0.1 M to about 3 M hydrogen peroxide.

10. The method of claim 1, wherein the component B comprises greater than about 3 units/mL of catalase.

11. The method of claim 1, wherein the component B comprises from about 30 units/mL to about 300,000 units/mL catalase.

12. The method of claim 1, wherein the component B comprises from about 1,000 units/mL to about 20,000 units/mL catalase.

13. The method of claim 1, wherein the component A and the component B are each characterized by a viscosity of less than 26 Pa·s at a shear rate of 1/s at 25° C.

14. The method of claim 1, wherein the component A and the component B are each characterized by a viscosity of less than 16 Pa·s at a shear rate of 1/s at 25° C.

15. The method of claim 1, wherein at least one of the component A and the component B is characterized by a viscosity of greater than 2 Pa·s at a shear rate of 1/s at 25° C.

16. The method of claim 1, wherein the component A and the component B are each characterized a viscosity of greater than 2 Pa·s at a shear rate of 1/s at 25° C.

17. The method of claim 1, wherein the hydrogen peroxide precursor is selected from the group consisting of carbamide peroxide, percarbonate salts or acids, polyvinylpyrrolidone (PVP) peroxide, and a combination thereof.

18. The method of claim 1, wherein the hydrogen peroxide precursor is selected from the group consisting of perborate salts or acids, metal peroxides, organic peroxide, inorganic peroxyacids or salts, and a combination thereof.

19. The method of claim 1, wherein the hydrogen peroxide precursor is an organic peroxide, and wherein the organic peroxide is a peracetate salt or acid.

20. The method of claim 1, wherein the hydrogen peroxide precursor comprises a peroxide-generating enzyme.

21. The method of claim 1, wherein at least one of the component A and the component B further comprising water, glycerol, a polyethylene glycol, a polyglycerol, or a combination thereof.

22. The method of claim 1, wherein at least one of the component A and the component B further comprises a thickener.

23. The method of claim 22, wherein the thickener is polyacrylic acid, gelatin, a polysaccharide, silica, or a combination thereof.

24. The method of claim 1, wherein the removing step comprises removing by mechanical means.

25. The method of claim 1, wherein the removing step at comprises removing by mechanical means other than tooth brushing.

26. The method of claim 1, wherein the removing step comprises removing at least a part of the calculus from the tooth with a dental scaler.

* * * * *